(12) United States Patent
Johnston (10) Patent No.: US 6,943,256 B2
(45) Date of Patent: Sep. 13, 2005

(54) CHIRAL ORGANIC COMPOUNDS AND METAL COORDINATION COMPLEXES THEREOF

(75) Inventor: Jeffrey N. Johnston, Bloomington, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 0 days.

(21) Appl. No.: 10/689,156

(22) Filed: Oct. 20, 2003

(65) Prior Publication Data

US 2004/0143118 A1 Jul. 22, 2004

Related U.S. Application Data

(63) Continuation of application No. PCT/US02/12609, filed on Apr. 22, 2002.
(60) Provisional application No. 60/285,631, filed on Apr. 20, 2001.

(51) Int. Cl.$^7$ .................. C07D 217/12; C07D 221/02
(52) U.S. Cl. .................. 546/143; 546/112; 546/139
(58) Field of Search .................. 546/112, 139, 546/143

(56) References Cited

U.S. PATENT DOCUMENTS 6,307,087 B1 * 10/2001 Buchwald et al. .......... 558/388
6,395,916 B1 * 5/2002 Buchwald et al. .......... 556/413

FOREIGN PATENT DOCUMENTS

WO    WO 99/06394    *  2/1999

* cited by examiner

*Primary Examiner*—Golam M M Shameem
(74) *Attorney, Agent, or Firm*—Dann, Dorfman, Herrell & Skillman, P.C.

(57) ABSTRACT

Disclosed are chiral organic compounds and metal coordination complexes thereof having $C_2$ symmetry.

7 Claims, 3 Drawing Sheets

CHIRAL ORGANIC COMPOUNDS AND METAL COORDINATION COMPLEXES THEREOF

This is a continuation of PCT Application No. PCT/US02/12609, filed Apr. 22, 2002, which claims priority of U.S. provisional Patent Application No. 60/285,631, filed Apr. 20, 2001. The entire disclosure of each of the aforementioned applications is incorporated by reference in the present application.

BACKGROUND OF THE INVENTION

The present invention relates to chiral organic compounds which do not necessarily contain asymmetric carbon atoms, and to methods of synthesizing such compounds. Compounds that have a plane of symmetry are superimposable on their mirror images and are, therefore, achiral. Compounds that are not achiral are chiral. The chiral compounds of the invention can be used, inter alia, as ligands to form metal coordination complexes of $C_2$ symmetry, which have utility as catalysts, pre-catalysts, and mediators of chemical reactions.

A chemical compound is said to have $C_2$ symmetry when, upon 180° rotation about a geometrical axis intersecting it, the compound in its rotated position is indistinguishable from the compound in its original, unrotated position.

$C_2$ symmetry has been noted as a preferred property of stereoselective catalysts and mediators. See, e.g., (a) Brintzinger, H. H.; Fischer, D.; Müllhaupt, R.; Rieger, B.; Waymouth, R. M. *Angew. Chem. Int. Ed. Engl.* 1995, 34, 1143, (b) Giardello, M. A.; Eisen, M. S.; Stern, C. L.; Marks, T. L. *J. Am. Chem. Soc.* 1993, 115, 3326, (c) Veghini, D.; Henling, L. M.; Burkhardt, T. J.; Bercaw, J. E. *J. Am. Chem. Soc.* 1999, 121, 564, (d) Hoveyda, A. H.; Morken, J. P. *Angew. Chem. Int. Ed. Engl.* 1996, 35, 1262.

A catalyst, as well known in the chemical arts, is a substance which participates in a chemical reaction but is restored to its original state at the end of the reaction. A pre-catalyst is a substance that is activated to form a catalyst. Such activation may be performed prior to the catalysis reaction, or may take place in situ. The activation may be an oxidation, reduction, radical initiation, Lewis acid-base interaction, or the like. A mediator, as well known in the chemical arts, is a substance which organizes or orients the reactants in a particular reaction without participating directly in the reaction. All catalysts are, therefore, mediators, but not every mediator is a catalyst.

Metallocene complexes having $C_2$ symmetry are especially well known for catalyzing and mediating stereoselective reactions. Enantioselective C—C and C—H bond formation mediated or catalyzed by chiral titanocene and zirconocene derivatives have been reviewed recently by Hoveyda and Morken in *Angew. Chem. Int. Ed. Engl.* 1996, 35, 1262–1284. In addition, metallocene complexes having $C_2$ symmetry are also well known as pre-catalysts.

There are, however, numerous disadvantages associated with the use of metallocene complexes. For example, these complexes are difficult to synthesize. The ethylene-bis-indenyl (ebi) ligand itself is not easily prepared. Also, enantiopure metallocene complexes cannot be made directly by methods currently known in the art. Once reacted with the metal, two tetrahedral (ebi)$ML_2$ complexes are formed, one of which is chiral and the other of which is a meso complex. In (ebi)$ML_2$, L represents a ligand. Representative structures of two ebi-metal complexes are shown below. Isomer A is chiral, while Isomer B has a plane of symmetry and is, therefore, a meso compound.

A

B

It is not always necessary to resolve the stereoisomers of the metal catalyst or mediator in order to carry out a stereochemically selective reaction. If, for example, one merely wished to synthesize a polymer diastereoselectively, a racemic mixture of the metal complex would be sufficient to control the relative stereochemistry of the reaction product. In order to control the absolute stereochemistry of the product, however, it is necessary to resolve the enantiomers of the catalyst or mediator. With respect to polymerizations, this becomes an issue in the synthesis of block copolymers.

The (ebi)$ML_2$ A and B complexes shown above may only be resolved by a reaction substituting a chiral ligand L* for one of the achiral ligands L in the chiral (ebi)$ML_2$ complex, thus producing two diastereomers, which may then be separated according to methods known in the art. After the separation, the desired diastereomer must be reacted further to replace L and L* with labile groups such as Cl⁻ in order to form a catalyst precursor. It is apparent that the necessity for such time-consuming and expensive procedures detracts from the general utility of metallocene catalysts and mediators.

Further, metallocene-type complexes are often unstable under desirable storage and reaction conditions. The instability extends to thermal interconversion of the structural isomers at temperatures as low as 100° C. for (ebi)$ZrCl_2$, for example.

Proposed substitutes for metallocene complexes include amidinates (see G. J. P. Britovsek, V. C. Gibson, D. F. Wass, *Angew. Chem. Int. Ed. Engl.,* 1999, 38, 428), and non-chiral β-diketimines (see A. Pfaltz, *J. Heterocycl. Chem.,* 1999, 36, 1437 and A. Pfaltz, *Synlett* 1999, 835.).

Therefore, despite the well-documented utility of $C_2$-symmetrical metallocene catalysts, pre-catalysts, and mediators for stereoselective synthesis, there is a significant need for the development of non-metallocene complexes that retain $C_2$ symmetry, yet offer a greater degree of accessibility to the stereodefined site or improved performance in terms of yield, turnover, specificity, or ease of handling.

SUMMARY OF THE INVENTION

Accordingly, in one aspect, the present invention provides chiral β-diketimines that do not necessarily contain any asymmetric carbon atoms. Also provided are methods for the synthesis of such compounds.

In another aspect, the invention provides metal complexes of the chiral β-diketimines of the invention, preferably metal complexes having $C_2$ symmetry. Also provided are methods for the synthesis of such complexes. Preferably, the metals are Group IV metals, and more preferably the metal is zirconium.

In another aspect of the invention, methods are provided for the catalysis of various chemical reactions using the compounds of the invention as catalysts, pre-catalysts, or mediators. Preferably, the reaction catalyzed is an olefin polymerization.

BRIEF DESCRIPTION OF THE DRAWINGS

FIGS. 1(a) (upper left) and 1(b) (lower left) are front views, and FIGS. 1(c) (upper right) and 1(d) (lower right) are side views.

FIG. 2(a), the ORTEP on the left, is a view bisecting the angle between the two $NMe_2$ ligands and illustrating the $C_2$ symmetry of the complex. FIG. 2(b), the ORTEP on the right, is rotated 90° about the z axis relative to FIG. 2(a) and emphasizes the distorted octahedral coordination of the zirconium atom.

DESCRIPTION OF THE PREFERRED EMBODIMENTS

The present invention relates to compounds of formula I, below, which are β-diketimines that have been desymmetrized by steric interactions.

(I)

In formula III and elsewhere hereinbelow, "BDK" represents the compound of formula I in ligand form.

In complexes of formula I, each of $R^1$, $R^2$, $R^3$, $R^6$, and $R^7$ independently represents a radical selected from hydrogen, halogen, alkyl, aryl, aralkyl, acyl, heterocyclo, cycloalkyl, and $SiR_aR_bR_c$, any of which radicals may optionally be substituted. In addition, $R^1$ and $R^2$ taken together may form a $=CR_aR_b$ group; or, $R^1$ and $R^2$, when taken together with the nitrogen atom to which they are attached, may form an unsubstituted or substituted heterocyclic ring stricture. Each of $R^4$ and $R^5$ represents a radical selected independently from halogen, alkyl, aryl, aralkyl, acyl, heterocyclo, cycloalkyl, and $SiR_aR_bR_c$, any of which radicals may optionally be substituted.

In addition, $R^3$ and $R^4$, when taken together with the carbon atoms to which they are attached, may form an unsubstituted or substituted ring structure.

Likewise, $R^5$ and $R^6$, when taken together with the carbon atoms to which they are attached, may form an unsubstituted or substituted ring structure.

$R_a$, $R_b$, and $R_c$ represent the same radicals as $R^1$ and $R^2$, above. Any ring structure including $R^3$ and $R^4$ or $R^5$ and $R^6$ is selected from the group consisting of cycloalkyl, aryl, or heterocyclic, any of which may be substituted or unsubstituted.

Preferred chiral β-diketimines are compounds of the formula II, below, wherein $R^1$, $R^2$, and $R^7$ are as defined above. These compounds are the product of a reaction between Isoquinoline and a 2-Amino Naphthalene (I and AN) and may be abbreviated as "IAN-amines," "IAN," or "IAN-H," as appropriate.

(II)

Other preferred compounds of the invention are those which comprise two BDK moieties, for example, formulae II(a), II(b), and II(c), below, wherein $R^{1a}$ is a variable of the same scope as $R^1$, and $R^1$ is as defined above, and wherein p is an integer from 0 to 50, preferably from 1 to 12, and more preferably from 1 to 4.

Compounds of formula I may act as bidentate ligands to form, under appropriate conditions and optionally together with other ligands, metal complexes, preferably complexes having $C_2$ symmetry.

$$(BDK)_r ML_{(n-2r)} \quad (III)$$

In compounds of formula III, M represents a metal atom, r represents an integer such that 2r is less than or equal to n, n represents an integer equal to the total number of coordination sites available on the atom M, and L represents a ligand or ligands which are unidentate or multidentate. When (n–2r) is greater than one, the ligands L need not be identical to each other; rather, each ligand L is independently selected.

Empirical formula IV applies when each ligand L is unidentate; manifestly, if one or more of L is multidentate, a slightly different empirical formula will apply. For example, if all of the ligands L are bidentate, the complex would best be described by formula III(a), below.

$$(BDK)_r ML_{(n-2r)/2} \quad (III(a))$$

Those of skill in the art can readily derive similar empirical formulae for other ligand denticities, and for combinations of ligands of varying denticities, based on the oxidation state and coordination number of the metal M, and the charge on the BDK and other ligands.

Compounds of Formula II also form metal-containing coordination complexes. These coordination complexes are of the formula IV $$(IAN)_r ML_{(n-2r)} \quad (IV)$$

wherein M, L, r, and n are as defined above. As in compounds of formula III, empirical formula IV applies when all ligands L are unidentate; again, if one or more of L is multidentate, formula IV will vary slightly.

Metal complexes of compounds of Formula I may have the structural formula V or VI, wherein M and L are as defined above. These compounds are of special interest when BDK is IAN. Also of special interest are metal complexes in which M is a Group IV metal, a metal in the +4 valence state, or particularly a metal with the tendency to form octahedral coordination complexes.

$$(BDK)_2 ML_2 \quad (V)$$

$$(BDK)ML_3 \quad (VI)$$

Advantageously, the compounds of formula I also form complexes with positive hydrogen ions, i.e., protons. Such complexes have utility as catalysts or mediators of stereodefined protonation reactions.

Furthermore, complexes of Formulae III, IV, V, and VI find utility as catalysts, pre-catalysts, and mediators of hydroaminations of alkynes and alkenes, including kinetic resolutions; as Lewis acid catalysts for carbon-carbon bond-forming reactions, including ene, aldol, Michael, and sigmatropic rearrangement-type reactions; as catalysts, pre-catalysts, and mediators for olefin polymerizations; and as catalysts for alkane and alkene oxidation reactions. Complexes of Formulae III, IV, V, and VI also find utility as catalysts, pre-catalysts, and mediators of the asymmetric, e.g., diastereoseletive or enantioselective, variations of the above-listed reactions.

The β-diketimine compounds of the present invention are unusual for being chiral without necessarily containing any asymmetric tetrahedral carbon atoms. The present invention specifically contemplates structural methods by which organic molecules may be rendered chiral without containing any asymmetric carbon atoms.

Figure 1:
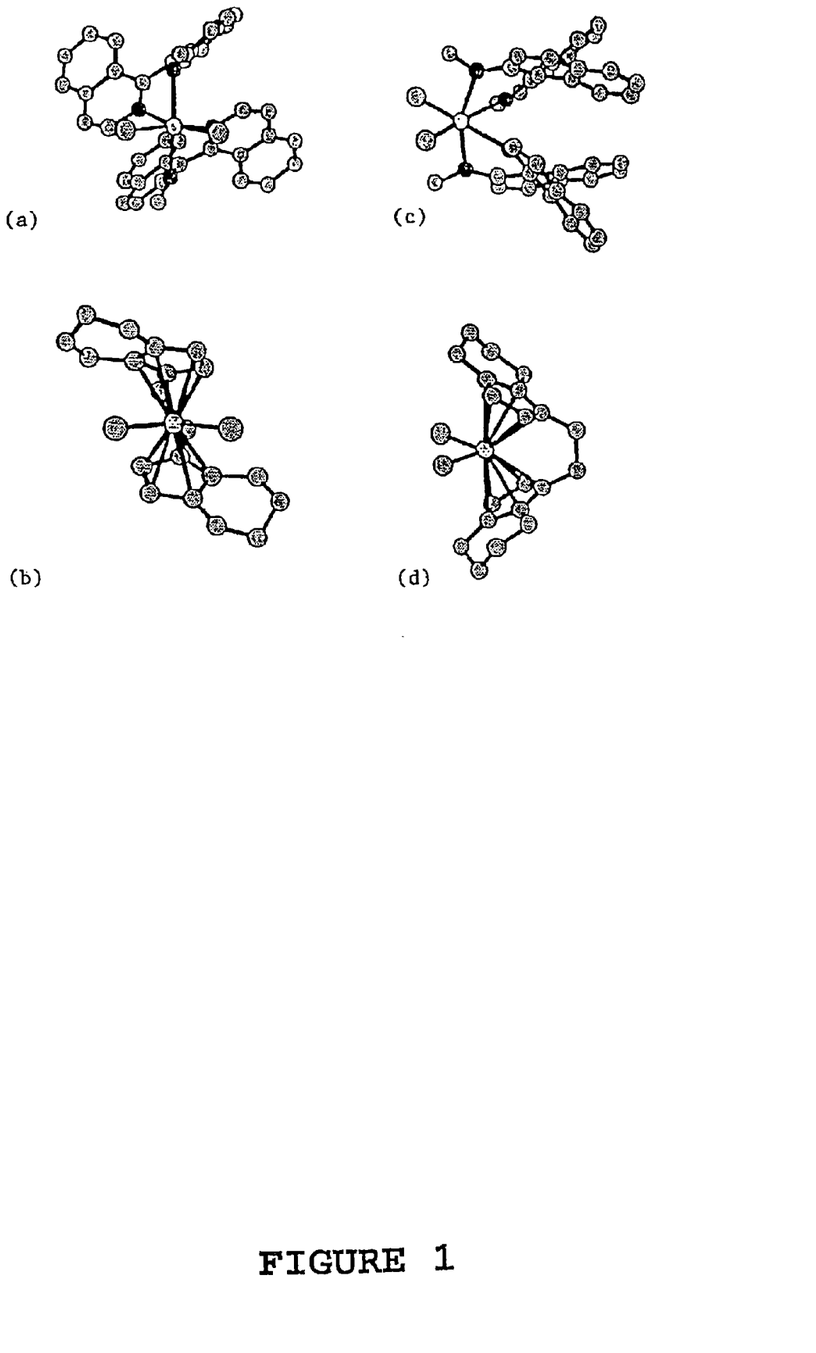
FIG. 1 contains four ORTEP (Oak Ridge Thermal Ellipsoid Program) renditions showing the structural similarities between $(IAN)_2Zr(NMe_2)_2$ and a metallocene polymerization catalyst.

The metal complexes of the present invention are characterized by $C_2$ symmetry. In FIG. 1, an ORTEP rendition comparing the structures of an IAN-amine complex with a metallocene polymerization catalyst, each molecule's axis of $C_2$ symmetry is clearly visible.

In considering formula I specifically, there is a steric interaction between the $R^4$ and $R^5$ residues, which, as a result, cannot both occupy the same space. The steric interaction between the $R^4$ and $R^5$ residues forces the two phenyl groups of the biphenyl moiety to rotate relative to one another. The handedness of the formula I molecule results from this disruption of the coplanarity of the two phenyl groups. In fact, the molecule may take one of two configurations, as shown below. The molecules of each configuration, arbitrarily designated Λ and Δ, are non-superimposable mirror images of each other, that is, enantiomers.

Λ

Δ

Interconversion of these enantiomers, or atropisomerization, may be effected by rotation of one bicyclic residue about the bond between the residues. It is expected, for example, that compounds of formula I in which one of $R^4$ or $R^5$ represents hydrogen will be useful as mediators of reactions with defined relative stereochemistry. These complexes are not expected to be resolvable, however, nor to be configurationally stable at reasonable reaction temperatures. The hypothesis is that a hydrogen in the $R^4$ or $R^5$ position does not represent a sufficient steric barrier to atropisomerization.

In formula II, it is apparent that the naphthalene and isoquinoline residues cannot lie in the same plane, due to steric interference between the hydrogen on carbon 8 of the naphthalene residue and the hydrogen on carbon 8 of the isoquinoline residue. The arbitrarily designated Λ and Δ isomers of the compounds of formula II are depicted below.

Λ

In order to examine the energy barrier to atropisomerization of compounds of formula II, albeit indirectly, diastereomeric α-methylbenzylamine derivatives in which $R^1$=H and $R^2$=CH(CH$_3$)(C$_6$H$_5$) were synthesized. The diastereomers were separated by silica gel chromatography, and the thermal integrity of each diastereomer was independently examined (Table 1). The configuration of each diastereomer was indefinitely stable to heating at reflux in toluene (110° C.). When the diastereomers were heated at reflux in xylenes (165° C.), atropisomerization was observed to the extent of 33% conversion after 5 hours. Both diastereomers equilibrated at indistinguishable rates to a 50:50 ratio of diastereomers upon prolonged heating at this temperature, suggesting it is unlikely that the atropisomerization barrier is affected by the stereochemistry at the $R^2$ chiral center. Therefore, compounds of formula II are also expected to retain their configurations up to about the same temperature.

TABLE 1

Atropisomerization of Enantiopure α-Methylbenzyl IAN-amines[a]

| Conditions | Relative Ratio of Λ Isomer[b] | Relative Ratio of Δ Isomer[b] |
| --- | --- | --- |
| toluene, 110° C., 4 h | 100 | 0 |
| xylenes, 145° C., 5 h | 67 | 33 |
| xylenes, 145° C., 17 h | 50 | 50 |

Notes:
[a]Progress was monitored by analysis of reaction aliquots by $^1$H-NMR spectroscopy at 400 MHz.
[b]Identity of enantiomers has been arbitrarily assigned.

Compounds of formula II are synthesized according to Scheme 1, below.

Scheme 1

In Scheme 1, LG represents a favorable leaving group. Those of skill in the art are familiar with a large variety of reactions designed to produce compounds with favorable leaving groups. Examples of favorable leaving groups include halogens and other conjugate bases of strong acids, for example substituted or unsubstituted p-nitrobenzoate groups and substituted or unsubstituted sulfonate groups. Preferably, the leaving group is a halogen, and most preferably chlorine.

structure. Preferably, the aluminum compound is a dialkyl aluminum halide or a trialkyl aluminum compound. More preferably, the aluminum compound is trimethyl aluminum.

The product compound of formula II shown in Scheme 1 maybe further reacted, by methods well known in the art, to substitute an $R^2$ group, wherein $R^2$ is as defined above, for the amine hydrogen.

An example of preferred reaction conditions is summarized in Scheme 1a, below.

Scheme 1a

The isoquinoline derivative and aminonaphthalene were coupled in the presence of aluminum compounds of varying

In Scheme 1a, 2-naphthol is reacted with a primary amine in a Bucherer reaction to form a 2-aminonaphthalene derivative, and isoquinoline is reacted with m-chloroperbenzoic acid (m-CPBA) in the presence of phosphorus oxychloride to yield 1-chloroisoquinoline. Both of these reactions are well known to the skilled artisan. Reaction of the aminonaphthalene and chloroisoquinoline in the presence of trimethyl aluminum yielded the desired C-coupled product of formula II. Again, the product compound of formula II shown in Scheme 1a may be further reacted to substitute an $R^2$ group, wherein $R^2$ is as defined above, for the amine hydrogen.

The synthesis depicted in Schemes 1 and 1a is convergent, that is, different moieties of the final product may be prepared in parallel before the final assembly step or steps. Convergent reaction schemes differ from traditional reaction schemes, in which one starting material is usually made to progress through a series of conversions in a linear, serial fashion. The greater economy and efficiency of the convergent scheme is manifest. Even given two syntheses with the same number of steps, the convergent synthesis will proceed more quickly, because some of the convergent reactions may be conducted in parallel.

Compounds of Formula IV may be synthesized according to Scheme 2.

Scheme 2

$$MX_n + rIAN\text{—}H + (n-2r)L \longrightarrow (IAN)_rML_{(n-2r)} + nHX$$

In Scheme 2, M is a metal atom, n is the number of coordination sites available on the metal atom, X is a leaving group, r is an integer such that $2r \leq n$, and L is another ligand or ligands. Scheme 2 assumes the L ligands are unidentate, but, as above, if one or more of L is multidentate, a different empirical formula will apply.

The reaction in Scheme 2 may also proceed in a stepwise fashion, for example with $MX_tL_u(IAN)_v$ as an intermediate, where t, u, and v are integers such that $t+u+2v=n$; L, X, and n are defined as above, and with the proviso that the empirical formula will vary if any ligand L is multidentate.

Compounds of Formula IV wherein r=2 may be synthesized according to Scheme 3, below.

Scheme 3

$$MX_4 + 2L + 2IAN\text{—}H \longrightarrow (IAN)_2ML_2 + 4HX$$

The reaction in Scheme 3 may also proceed in a stepwise fashion, for example with $ML_tX_u(IAN)_v$ as an intermediate, where L, X, t, u, and v are as defined above, and with the usual proviso that the empirical formula would be different if any of L were multidentate. Significantly, the conditions required to carry out a reaction according to Scheme 3 may be sufficiently mild that atropisomerization of the IAN enantiomers is unlikely to occur.

One such compound, $(IAN)_2Zr(NMe_2)_2$, was synthesized in quantitative yield in toluene at 80° C. according to the method of Scheme 3. Crystals suitable for X-ray diffraction analysis were grown from the reaction mixture. Surprisingly, each metal complex contains two IAN ligands of the same chirality. Without wishing to be bound to any hypothesis, it is believed that the chirality of the first IAN ligand to bind to the zirconium determines the chirality of the next IAN to be bound. It is also believed that the mechanism for this selection may include a through-bond or a through-space interaction favoring identical chirality for the second-bound IAN ligand.

Figure 2:
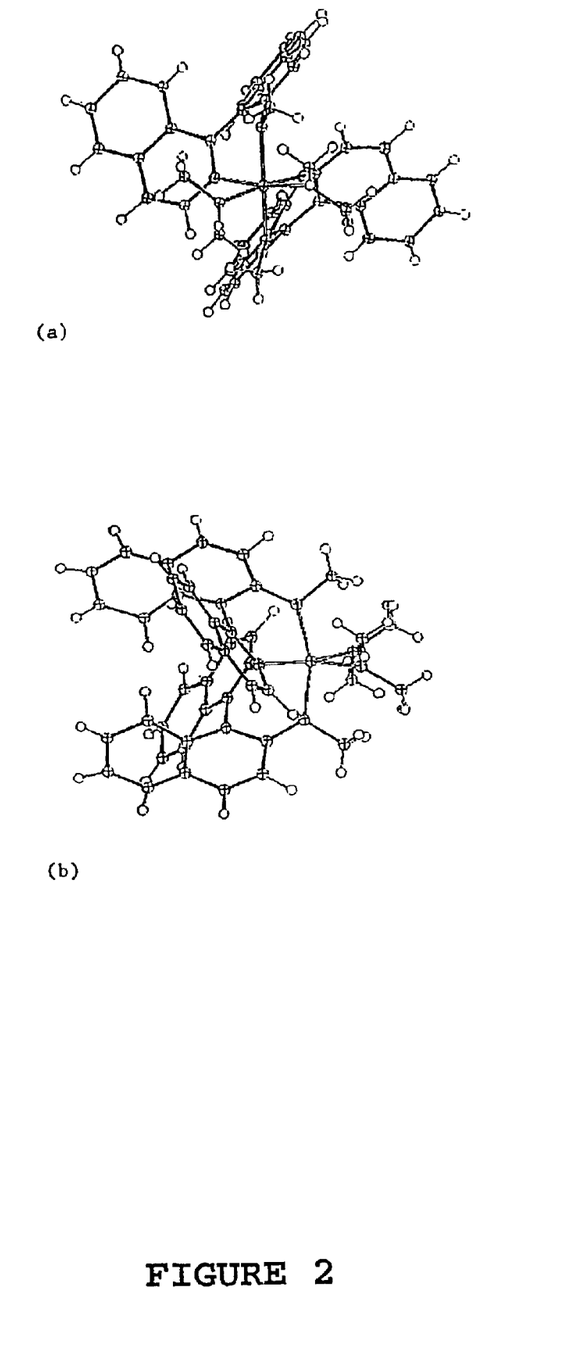
FIG. 2 is an ORTEP (Oak Ridge Thermal Ellipsoid Program) rendition of the crystal structure of $(Me-IAN)_2Zr(NMe_2)_2$, a compound of the present invention.

FIG. 2 depicts the ORTEP rendition of $(IAN)_2Zr(NMe_2)_2$. In FIG. 2(a), the $C_2$ symmetry of $(IAN)_2Zr(NMe_2)_2$ is apparent. The $C_2$ axis is perpendicular to the plane of the page. In FIG. 2(b), the distortions to the octahedral core of the complex are apparent. In the meridional plane, the bond lengths from the Zr atom to the $(NMe_2)$ nitrogens are shorter than the metal bonds to the isoquinoline nitrogens, consistent with the negative charge on the $(NMe_2)$ nitrogens.

In addition, complexes of Group IV metals in their +4 valence states are typically square planar. This is in harmony with the lengths of the metal bonds to the negatively charged amido nitrogens on the IAN ligand relative to those on the $(NMe_2)$ ligands. The metal bonds to the axial IAN amido nitrogens are notably longer and therefore weaker than the metal bonds to the meridional $(NMe_2)$ ligands. It also appears that the bite angle of the IAN ligand has caused a significant deviation from perpendicularity in the axial bonds.

Notwithstanding these observations, and still without wishing to be held to any particular hypothesis, it is conjectured that the overall $C_2$ symmetry of the molecule will have the greatest significance to its stereodefined reactivity.

The catalyst, pre-catalyst, and mediator complexes of the invention may be used in supported or unsupported form. Supporting a metal complex on a solid material is a well-known method for increasing the economy of a reaction by using less of the metal complex, or for creating beneficial structural and/or electronic interactions between the metal complex and the support.

Typical methods of preparing supported catalysts are well known to those skilled in the art. The metal complexes of the present invention may be chemically bound to a support, for example, by reacting a substituent on the metal complex with the support. Any means of supporting the metal complexes which is sufficient to maintain the association between the complex and the support under reaction conditions is appropriate, however. For example, a slurry of the support in a solution of the metal complex may be dried by evaporation, or freeze-dried. The metal complexes may also be impregnated into a support material by methods well known in the art.

Typical support materials include silica, titania, zirconia, alumina, thoria, silicon carbide, carbon, aluminosilicates, aluminophosphates, clays, and mixtures thereof. A polymer, such as polytetrafluoroethylene or a polyolefin, may also be employed. The support material may be in granular, agglomerated, pelletized, or any other physical form.

The supported or unsupported metal complexes can be used as isolated, or in cases where size and shape of the material is dictated by the requirements of the reactor equipment employed in its subsequent use, the catalyst can be processed or fabricated into particles of various sizes and shapes before use by grinding, pelletizing, briquetting, tabulating, or shaping in other ways as required.

The metal complexes of the invention which are catalysts, pre-catalysts, and mediators may require a catalyst activator in order to realize their activity. Appropriate activators include, without limitation, alumoxanes and activators capable of ionizing the metal complex, also referred to herein as "ionic activators".

The alumoxane activator may be of the formula:

$$R_2AlO(RAlO)_pAlR_2$$

wherein each R is independently selected from the group consisting of C1–C20 hydrocarbyl radicals and p is from 0 to 50; preferably, R is a C1–C4 alkyl radical and p is from 5 to 30. Methylalumoxane (or "MAO") is a preferred alumoxane.

Activation with alumoxane generally requires a molar ratio of aluminum in the activator to metal in the pre-catalyst from 20:1 to 1000:1. Preferred ratios are from 50:1 to 250:1.

Ionic activators which are readily available commercially include N,N-dimethylaniliumtetrakispentafluorophenyl borate; triphenylnethylium tetrakispentafluorophenyl borate; and trispentafluorophenyl boron.

Without wishing to be held to any theory, it is believed that the ionic activator abstracts one or more ligands so as to ionize the catalyst center into a cation, but not to covalently bond with the catalyst. The ionic activator may also provide sufficient distance between the catalyst and the ionizing activator to permit a polymerizable olefin to enter the resulting active site.

The metal complexes of the present invention are used to advantage as catalysts, pre-catalysts, and mediators of olefin polymerization. Preferred monomers for olefin polymerization include ethylene and C3–C12 alpha olefins which are unsubstituted or substituted by up to two C1–C6 alkyl radicals; C8–C12 vinyl aromatic monomers which are unsubstituted or substituted by up to two substituents selected from the group consisting of C1–C4 alkyl radicals; and C4–C12 straight chained or cyclic diolefins which are unsubstituted or substituted by a C1–C4 alkyl radical. Illustrative non-limiting examples of such alpha-olefins are one or more of propylene, 1-butene, 1-pentene, 1-hexene, 1-octene, and 1-decene, styrene, alpha methyl styrene, p-t-butyl styrene, and the constrained-ring cyclic olefins such as cyclobutene, cyclopentene, dicyclopentadiene norbornene, alkyl-substituted norbornenes,alkenyl-substituted norbornenes, and the like (e.g. 5-methylene-2-norbornene and 5-ethylidene-2-norbornene, bicyclo-(2,2,1)-hepta-2,5-diene).

In most instances, the olefin polymerization advantageously takes place at conditions known in the prior art for Ziegler-Natta or Karminsky-Sinn type polymerization reactions, i.e., temperatures from 0–250° C. and pressures from atmospheric to 3000 atmospheres. Suspension, solution, slurry, gas phase or high pressure, whether employed in batch or continuous form or under other process conditions, including the recycling of condensed monomers or solvent, is optionally employed. A support is preferably employed when the catalysts are used in a gas phase polymerization process. Such supported catalysts are preferably not affected by the presence of liquid aliphatic or aromatic hydrocarbons such as are optionally present when using of condensation techniques in a gas phase polymerization process.

The metal complexes of the invention are optionally also utilized in combination with at least one additional homogeneous or heterogeneous polymerization catalyst in separate reactors connected in series or in parallel to prepare polymer blends having desirable properties.

Furthermore, the compounds of the invention, and the complexes of the invention wherein the atom complexed is a metal or a proton, are used advantageously as catalysts, pre-catalysts, and mediators in stereodefined alkylation and protonation reactions.

Unless otherwise indicated, the term "alkyl" as employed herein alone or in combined form, e.g., haloalkyl or aralkyl, includes both straight and branched chain hydrocarbons containing 1 to 20 carbons, preferably 1 to 10 carbons, more preferably 1 to 8 carbons, in the normal chain. Examples of alkyl groups include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Each alkyl group may optionally be substituted with 1 to 4 substituents which may include halo, $CF_3$, alkoxy, aryl, aryloxy, aralkyl, aralkyloxy, alkenyl, cycloalkyl, amino, monoalkyl amino, dialkyl amino, hydroxy, acyl, heterocyclo, heterocyclooxy, heterocycloalkoxy, aryloxyaryl, alkylamido, alkanoylamino, arylcarbonylamino, nitro, cyano, thiol, and/or alkylthio.

The normal carbon chain of any alkyl group herein may optionally be interrupted by one or more heteroatoms, i.e., N, O, S, Se, P, As, and Si.

Unless otherwise indicated, the term "cycloalkyl" as employed herein alone or in combined form includes saturated or unsaturated cyclic hydrocarbon groups containing 1 to 3 rings, that is, monocyclic alkyl, bicyclic alkyl and tricyclic alkyl. Cycloalkyl groups may contain a total of 3 to 20 carbons forming the ring(s), preferably 3 to 10 carbons forming the ring(s), and may optionally be fused to 1 or 2 aromatic rings as described for aryl, below. Unsaturated cycloalkyl groups may contain one or two double bonds, or one triple bond. Cycloalkyl groups include cyclopropyl, cyclobutyl, cyclopentyl, cyclohexyl, cycloheptyl, cyclooctyl, cyclodecyl and cyclododecyl, cyclopentenyl, cyclohexenyl, cycloheptenyl, cyclooctenyl, cyclohexadienyl, cycloheptadienyl, adamantyl, decahydronaphthyl, bicyclo[3.3.2]decanyl, and the like.

Each cycloalkyl group may be optionally substituted with 1 to 4 substituents such as halogen, alkyl, alkoxy, hydroxy, aryl, aryloxy, aralkyl, cycloalkyl, alkylamido, alkanoylamino, oxo, acyl, arylcarbonylamino, amino, monoalkyl amino, dialkyl amino, nitro, cyano, $CF_3$, thiol and/or alkylthio, and/or any of substituents for alkyl groups described above.

Unless otherwise indicated, the term "aryl" as employed herein alone or in combined form, e.g., aralkyl, refers to monocyclic and bicyclic aromatic groups containing 6 to 10 carbons in the ring portion. Examples of aryl groups include phenyl or naphthyl, such as 1-naphthyl and 2-naphthyl, or indenyl. Aryl groups may optionally include one to three additional rings fused to a cycloalkyl ring or a heterocyclic ring.

Aryl groups may be optionally substituted through available carbon atoms with 1, 2, or 3 groups selected from halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, monoalkyl amino, or dialkyl amino.

The term "aralkyl" as used herein refers to an aryl group, as defined above, bonded to the compound through an alkyl moiety, such as a benzyl group, for example. An aralkyl group may be optionally substituted with any group described herein as an aryl or alkyl substitutent.

As used herein, the tern "acyl" refers to the radical of an organic acid, in which the OH of the carboxyl group has been removed. The acyl group may be alkyl, alkenyl, alkynyl, aryl, aralkyl, cycloalkyl, or heterocyclic, and may be substituted with any of the alkyl, aryl, or heterocyclic substituents listed herein.

The terms "heterocyclo", "heterocyclic" and "heterocycle" as used herein alone or in combined form refer to an optionally substituted, aromatic or non-aromatic cyclic group, which, for example, is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms. The heterocyclic group may be attached at any heteroatom or carbon atom.

Examples of suitable monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrinidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, triazolyl, and the like.

Examples of suitable bicyclic heterocyclic groups include ildolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofiryl, thienopyridyl, thienothienyl, and the like.

Examples of suitable substituents for heterocyclic groups include one or more of any of the alkyl substituents set forth hereinabove alkyl groups as described above or one or more groups described above as alkyl or aryl substituents. Also suitable are aryl groups and smaller heterocycles, such as epoxides and aziridines.

As used herein, the term "ring structure" refers to a moiety comprising a cycloalkyl, aryl, or heterocyclic group. A ring structure may br unsubstituted or substituted with any of the substituents as defined above for cycloalkyl, aryl, and heterocyclic groups.

In addition, as used herein, any alkyl, aryl, aralkyl, acyl, heterocyclo, or cycloalkyl group, or any ring structure, may optionally be substituted by a residue of a compound of the present invention of formula I, or by a residue of a compound of the present invention of formula II.

The term "heteroatom" as used herein includes oxygen, sulfur, nitrogen, phosphorus, selenium, arsenic, boron, and silicon. The heteroatoms may also optionally be oxidized or quaternized.

The term "halogen" or "halo" as used herein alone or in combined form refers to fluorine, chlorine, bromine, and iodine.

The term "metal" as used herein includes any element whose atoms may be present as positive ions in aqueous solution.

In the structures and formulae used herein, when no relative configuration is specified in a chemical structure or formula, either or both enantiomers or any combination of stereoisomers may be present.

The invention is further described by the following working examples, which include preferred embodiments of the invention. All temperatures are in degrees centigrade (° C.) unless otherwise indicated. These examples are intended to be illustrative only, and do not limit the invention.

EXAMPLE 1

Preparation of 2-(N-methylamino)naphthalene

The methods of Morgan et al. and Terenin et al. were employed (Morgan, G. T.; Evers, F. P. *J. Chem. Soc.* 1919, 115, 1140–1145; Terenin, V.; Geraskimerko, A.; Kurts, A.; Bundel, Y. *Zhurnal Organicheskoi Khimii,* 1990, 26, 2188–2191. Translated in *J. Org. Chem. USSR Eng.,* 1991, 1890–1896).

2-Naphthol (5.1515 g, 0.036 mol) ammonium chloride (2.6082 g, 0.383 mol), and 40% methylarnine in $H_2O$ (133.6 g, 1.16 mol) and ethanol (10 mL) were combined in a Parr reactor. The sealed reactor was heated by heating tape to 200° C. for 20 hours. After cooling to room temperature, EtOAc and $H_2O$ were added. The phases were separated and the organic phase was washed with 6 M NaOH, dried ($Na_2SO_4$, filtered, and concentrated. The brown liquid was purified by silica gel chromatography (5% EtOAc in hexanes) to fuirnish the product (4.2292 g, 75%) as a red-brown liquid. Alternatively, the product may be purified by vacuum distillation (8 mm, 160–163° C.) to give a colorless liquid that rapidly darkens upon exposure to air:

IR (film) 3419, 1632 $cm^{-1}$; $^1H$ NMR (400 MHz, $CDCl_3$) d 7.69 (d, J=8.1 Hz, 1H), 7.66 (d, J=8.1 Hz, 1H), 7.64 (d, J=8.6 Hz, 1H), 7.38 (ddd, J=8.1, 8.1, 1.2 Hz, 1H), 7.21 (ddd, J=8.1, 8.1, 1.2 Hz, 1H), 6.89 (dd, J=8.8, 2.3 Hz, 1H), 6.81 (d, J=2.3 Hz, 1H), 3.88 (br s, 1H), 2.95 (s, 3H); $^{13}C$ NMR (100 MHz, $CDCl_3$) ppm 147.2, 135.5, 129.1, 127.9, 127.7, 126.6, 126.2, 122.2, 118.1, 104.0, 31.0; HRMS (CI, $CH_4$) Exact mass calcd for $C_{11}H_{11}N$ $[M]^+$, 157.0891. Found 157.0897.

EXAMPLE 2

General Method for the Preparation of N-Substituted Aminonaphthalenes

N-Substituted aminonaphthalenes wherein $R^1$ is as defined above are conveniently prepared from naphthol triflate and the requisite amine mediated by a palladium catalyst. See, e.g., Wolfe, J. P., Wagaw, S., Marcoux, J.-F., Buchwald, S. L. *Acc Chem. Res.* 1998, 31, 805; Hartwig, J. F. *Pure Appl. Chem.* 1999, 71, 1417; and Yang, B. H. and Buchwald, S. L., *J. Organomet. Chem.* 1999, 576, 125.

EXAMPLE 3

Preparation of 1-Chloroisoquinoline

The method is an adaptation of those employed by Ferrer et al. and Alcock et at. (Ferrer, M.; Messeguer, A. *Tetrahedron* 1997, 53, 15877–15888; Alcock, N. W.; Brown, J. M.; Hulries, D. I. *Tetrahedron Asymmetry,* 1993, 4, 743–756).

m-CPBA (18.0 g, 0.104 mol) was added to a solution of isoquinoline (9.60 g, 0.074 mol) in $CH_2Cl_2$ at 0° C. After stirring for 3 h, $Na_2SO_3$ was added. The mixture was washed with sat'd $K_2CO_3$, dried ($MgSO_4$), and filtered. Solvent removal delivered a tan powder (9.30 g) that was used immediately in the next step.

Analytically pure material was obtained by silica gel chromatography (8% MeOH in CH$_2$Cl$_2$); white powder: mp 103–105° C.; IR (film) 3058, 1637 cm$^{-1}$; $^1$H NMR (400 MHz, CDCl$_3$) d 8.76 (s, 1H), 8.13 (dd, J=7.1, 1.7 Hz, 1H), 7.79 (d, J=7.7 Hz, 1H), 7.72 (d, J=7.7 Hz, 1H), 7.67 (d, J=7.1 Hz, 1H), 7.63 (ddd, J=7.1, 7.1, 1.7 Hz, 1H), 7.59 (ddd, J=7.1, 7.1 1.7 Hz, 1H); $^{13}$C NMR(100 MHz, CDCl$_3$) ppm 137.1, 136.4, 129.8, 129.3, 129.1, 126.9 (2c), 125.2, 124.5; HRMS (CI, CH$_4$) Exact mass calcd for C$_9$H$_7$NO [M]$^+$, 145.0528. Found 145.0528.

A dichloromethane solution (60 mL) of the N-oxide (9.30 g, 0.064 mol) was treated with phosphorous oxychloride (18.5 mL, 0.199 mol) and warmed to reflux temperature for 2 h. The reaction mixture was cooled and poured directly into an ice-water mixture. Ammonium hydroxide was added until the solution was alkaline. The layers were separated, and the aqueous layer was further extracted with ethyl acetate. The combined organic layers were dried (MgSO$_4$), filtered, and concentrated to a brown liquid that afforded 1-chloroisoquinoline (7.66 g, 63%) as a low-melting crystalline solid after vacuum distillation (2 mm, 86–87° C.): mp 41–43° C.; IR (film) 3056, 1623 cm$^{-1}$; $^1$H NMR (400 MHz, CDCl$_3$) d 8.33 (d, J=8.3 Hz, 1H), 8.27 (d, J=5.6 Hz, 1H), 7.84 (d, J=8.3 Hz, 1H), 7.74 (ddd, J=8.3, 8.3, 1.2 Hz, 1H), 7.68 (ddd, J=8.3, 8.3, 1.2 Hz, 1H), 7.59 (d, J=5.6 Hz, 1H); $^{13}$C NMR(100 Mz, CDCl$_3$) ppm 151.9, 141.7, 138.0, 131.4, 128.8, 127.2 (2c), 126.7, 121.0; HRMS (CI, CH$_4$) Exact mass calcd for C$_9$H$_6$ClN [M]$^+$, 163.0189. Found 163.0143.

EXAMPLE 4

Preparation of (1-Isoquinolin-1-yl-naphthalen-2-yl)-methyl-amine

2-Methylaminonaphthalene (2.4667 g, 0.016 mol), 1-chloroisoquinoline (2.5523 g, 0.016 mol), and Et$_2$AlCl (24.0 mL, 1.0 M in hexanes) were combined in benzene and refluxed for 48 h. After cooling to room temperature, the solution was added to 6 M NaOH. Sodium potassium tartrate was added and the mixture was stirred for 15 min. The layers were separated and the aqueous layer was further extracted with ethyl acetate. The combined organic layers were dried (MgSO$_4$), filtered and concentrated. The brown oil was purified by silica gel chromatography (20% EtOAc in hexanes) to ftnnish the product (3.3438 g, 75%) as a yellow solid:

mp 132–134° C.; IR (film) 3428, 1618 cm$^{-1}$; $^1$H NMR (400 MHz, CDCl$_3$) d 8.78 (d, J=5.6 Hz, 1H), 7.96 (d, J=8.2 Hz, 1H), 7.94 (d, J=8.5 Hz, 1H), 7.80 (d, J=5.6 Hz, 1H), 7.79 (d, J=9.9 Hz, 1H), 7.71 (ddd, J=8.2, 8.2, 1.1 Hz, 1H), 7.54 (d, J=8.5 Hz, 1H), 7.41 (ddd, J=8.2, 8.2, 1.1 Hz, 1H), 7.26 (d, J=9.9 Hz, 1H), 7.21–7.12 (m, 2H), 6.79 (d, J=8.2 Hz, 1H), 3.81 (br s, 1H), 2.87 (s, 3H); $^{13}$C NMR(100 MHz, CDCl$_3$) ppm 159.1, 145.3, 143.6, 137.1, 134.0, 130.8, 130.3, 128.9, 128.2, 127.8 (2c), 127.3 (2c), 126.7, 123.9, 121.9, 120.6, 116.1, 113.7,31.2; HRMS (CI, CH$_4$) Exact mass calcd for C$_{20}$H$_{16}$N$_2$ [M]$^+$284.1313. Found 284.1324.

EXAMPLE 5

Preparation of (S)-2-(α-Methylbenzylamino) naphthalene

2-Naphthol (0.5591 g, 3.9 mmol) ammonium chloride (0.1851 g, 3.5 mmol), and (S)-α-methylbenzylamine (2.8 mL, 21.7 mmol) and ethanol (3.0 mL) were combined in a Kantes sealed tube, which was heated in a Wood's Metal bath at 200° C. for 48 hours. After cooling to room temperature, the mixture was concentrated in vacuo. Excess (S)-amine was removed via vacuum distillation. The residue was diluted with EtOAc, washed with 6 M NaOH, dried (Na$_2$SO$_4$), filtered, and concentrated. The brown liquid was purified by silica gel chromatography (10% EtOAc in hexanes) to furnish the product (0.5454 g, 57%) as a tan solid: mp 73–75° C.; IR (film) 3411, 1629 cm$^{-1}$; $^1$H NMR (400 MHz, CDCl$_3$) δ 7.73 (d, J=8.2 Hz, 1H), 7.68 (d, J=8.8 Hz, 1H), 7.57 (d, J=8.2 Hz, 1H), 7.49 (d, J=7.7 Hz, 2H), 7.4–7.23 (m, 5H), 6.96 (dd, J =8.8, 2.1, 1H), 6.72 (d, J=2.1 Hz, 1H), 4.69 (q, J=6.6 Hz, 1H), 4.27 (br s, 1H), 1.64 (d, J=6.6 Hz, 3H); $^{13}$C NMR(100 MHz, CDCl$_3$) ppm 145.2, 145.1, 135.4, 129.1, 129.0 (2c), 127.9, 127.7, 127.3, 126.5, 126.3, 126.2 (2c), 122.2, 118.3, 106.0, 53.8, 25.2; HRMS (CI, CH$_4$) Exact mass calcd for C$_{20}$H$_{16}$N$_2$ [M]$^+$247.1361. Found 247.1370.

EXAMPLE 6

Preparation of 1,1'-(S)-2-(α-Methylbenzylamino) naphthylisoquinoline

A benzene solution (0.5 mL) of (S)-2-(α-methylbenzylamino)naphthalene (18.6 mg, 75 μmol) and 1-chloroisoquinoline (12.4 mg, 75 μmol) was treated with Et$_2$AlCl (140 μL, 1.0 M in hexanes) and refluxed for 3 d. The solution was cooled, poured into 6 M NaOH, extracted with EtOAc, dried (MgSO$_4$), and concentrated. The residue was purified by silica gel chromatography (20% EtOAc in hexanes) to furnish the pure diastereoisomers. Diastereomer A: brown oil (3.7 mg, 13%), R$_f$=0.23 (20% EtOAc/hexanes); IR (film) 3421, 1620 cm$^{-1}$; $^1$H NMR (400 MHz, CDCl$_3$) δ 8.86 (d, J=5.8 Hz, 1H), 7.99 (d, J=8.2 Hz, 1H); 7.82 (d, J=5.7 Hz, 1H), 7.76–7.71 (m, 3H), 7.62 (d, J=8.3 Hz, 1H), 7.45 (ddd, J=7.5, 7.5, 1.1 Hz, 1H), 7.38 (d, J=7.3 Hz, 2H), 7.32 (d, J=7.3 Hz, 2H), 7.22 (d, J=7.3 Hz, 2H), 7.20–7.12 (m, 2H), 7.00 (d, J=9.0 Hz, 1H), 6.84 (dd, J=7.5, 1.4 Hz, 1H), 4.69 (q, J=5.8 Hz, 1H), 4.11 (br s, 1H), 1.24 (d, J=6.7 Hz, 3H); $^{13}$C NMR (100 MHz, CDCl$_3$) ppm 159.1, 145.4, 143.7, 143.4, 137.1, 134.0, 130.8, 130.0, 128.9 (2c), 128.1, 127.8 (2c), 127.7, 127.3, 127.0, 126.6, 126.1 (2c), 124.1, 122.0, 120.6, 115.6, 53.7, 25.4; HRMS (CI, CH$_4$) Exact mass calcd for C$_{27}$H$_{22}$N$_2$ [M]$^+$, 374.1783. Found 374.1777.

Diastereomer B: brown oil (3.4 mg, 12%), $R_f$=0.14; IR (film) 3419, 1620 cm$^{-1}$; $^1$H NMR (400 MHz, CDCl$_3$) δ 8.84 (d, J=5.6 Hz, 1H), 8.00 (d, J=8.2 Hz, 1H), 7.83 (d, J=5.7 Hz, 1H), 7.77–7.70 (m, 2H), 7.55 (d, J=8.5 Hz, 1H), 7.45 (dd, J=7.5, 7.5 Hz, 1H), 7.24–7.10 (m, 5H), 7.02 (d, J=9.0 Hz, 1H), 6.78 (d, J=8.1 Hz, 1H), 4.69 (q, J=6.6 Hz, 1H), 4.09 (br s, 1H), 1.32 (d, J=6.7 Hz, 3H); $^{13}$C NMR (100 MHz, CDCl$_3$) ppm 159.2, 145.7, 143.6, 143.4, 137.2, 133.9, 130.8, 129.9, 128.9, 128.7 (2c), 128.1, 128.0, 127.7, 127.4, 127.3, 127.0, 126.6, 125.9 (2c), 124.1, 122.0, 120.6, 115.7, 53.7, 25.2; HRMS (CI, CH$_4$) Exact mass calcd for C$_{27}$H$_{22}$N$_2$ [M]$^+$, 374.1783. Found 374.1786.

EXAMPLE 6

Preparation of 2,6-iPr$_2$Ph-IAN amine 2-(N-(2,6-iPr$_2$Ph)-amino)naphthalene (95.0 mg, 313 mol) and 1-chloroisoquinoline (53.8 mg, 329 mol) were dissolved in toluene (4.0 mL). AlMe$_3$ (0.24 mL, 2.0 M in toluene, 480 mol) was added in one portion via syringe and the solution was heated at reflux for 48 h. Then, the solution was cooled to room temperature and added to 6 M aqueous NaOH. Sodium potassium tartrate and EtOAc were added and the mixture was stirred for 30 min. The layers were separated and then the aqueous phase was further extracted with EtOAc. The combined organic phases were dried (MgSO$_4$), filtered, and concentrated in vacuo. Purification via flash column chromatography on silica gel (2% EtOAc in hexanes) gave the desired product (70.4 mg, 52%) as a yellow powdery solid: mp 171.5–172.6° C.; $R_f$=0.18 (20% EtOAc in hexanes); IR (neat) 3412, 2962, 1620 cm$^{-1}$; $^1$H NMR (400 MHz, CDCl$_3$) 8.82 (d, J=5.6 Hz, 1H), 7.96 (d, J=8.5 Hz, 1H), 7.80 (d, J=5.8 Hz, 1H), 7.77–7.71 (m, 4H), 7.46 (ddd, J=8.1, 8.1, 1.1 Hz, 1H), 7.23 (d, J=7.5 Hz, 1H), 7.21–7.15 (m, 3H), 7.12 (d, J=7.5 Hz, 1H), 6.95–6.92 (m, 1H), 6.71 (d, J=9.0 Hz, 1H), 5.14 (s, 1H), 3.29 (sept, J=6.8 Hz, 1H), 3.00 (sept, J=6.8 Hz, 1H), 1.15 (d, J=6.8 Hz, 3H), 1.08 (d, J=6.8 Hz, 3H), 1.06 (d, J=6.8 Hz, 3H), 0.67 (d, J=6.8 Hz, 3H); $^{13}$C NMR (100 MHz, CDCl$_3$) 159.2, 147.9, 147.6, 143.9, 143.6, 137.2, 135.4, 134.1, 130.9, 130.0, 128.9, 128.2, 127.8, 127.7, 127.4, 127.3, 126.9, 124.2, 124.1, 123.9, 122.2, 120.7, 116.1, 115.2, 28.5, 28.4, 24.5, 24.3, 23.4, 23.0; HRMS (CI, CH$_4$): Exact mass calcd for C$_{31}$H$_{30}$N$_2$ [M]$^+$ 430.2409, found 430.2404.

EXAMPLE 7

Preparation of 2,6-Me$_2$Ph-IAN amine

—(N-(2,6-Me$_2$Ph)-amino)naphthalene (129.8 mg, 525 mol) and 1-chloroisoquinoline (85.9 mg, 525 mol) were dissolved in toluene (5.0 mL). AlMe$_3$ (0.40 mL, 2.0 M in toluene, 800 mol) was added in one portion via syringe and the solution was heated at reflux for 24 h. Then, the solution was cooled to room temperature and added to 6 M aqueous NaOH. Sodium potassium tartrate and EtOAc were added and the mixture was stirred for 30 min. The layers were separated and then the aqueous phase was further extracted with EtOAc. The combined organic phases were dried (MgSO$_4$), filtered, and concentrated in vacuo. Purification via flash column chromatography on silica gel (10% EtOAc in hexanes) gave the desired product (170.1 mg, 87%) as a yellow powdery solid: mp 186.5–187.5° C.; $R_f$=0.08 (20% EtOAc in hexanes); IR (neat) 3398, 3050, 1620 cm$^{-1}$; $^1$H NMR (400 MHz, CDCl$_3$) 8.83 (d, J=5.6 Hz, 1H), 7.96 (d, J=8.2 Hz, 1H), 7.81–7.69 (m, 5H), 7.45 (dd, J=7.9, 7.9 Hz, 1H), 7.22–7.18 (m, 2H), 7.05 (d, J=5.2 Hz, 2H), 7.05–7.03 (m, 1H), 6.94 (d, J=8.1 Hz, 1H), 6.75 (d, J=8.9 Hz, 1H), 5.39 (s, 1H), 2.17–2.14 (br s, 6H); $^{13}$C NMR (100 MHz, CDCl$_3$) 159.2, 143.5, 142.3, 138.1, 137.1, 135.9 (2C), 134.1, 130.8, 130.0, 128.7 (3C), 128.2, 128.0, 127.8 (2C), 127.3, 126.8, 125.8, 124.2, 122.4, 120.7, 117.1, 115.4, 18.7 (2C); HRMS (CI, CH$_4$): Exact mass calcd for C$_{27}$H$_{22}$N$_2$ [M]$^+$ 374.1783, found 374.1778.

EXAMPLE 8

Preparation of (2,4,6-Me$_3$Ph)-IAN amine

—(N-(2,4,6-Me$_3$Ph)-amino)naphthalene (181.0 mg, 693 mol) and 1-chloroisoquinoline (112.7 mg, 689 mol) were dissolved in toluene (4.0 mL). AlMe$_3$ (0.53 mL, 2.0 M in toluene, 1.06 mmol) was added in one portion via syringe and the solution was heated at reflux for 4 h. Then, the solution was cooled to room temperature and added to 6 M aqueous NaOH. Sodium potassium tartrate and EtOAc were added and the mixture was stirred for 30 min. The layers were separated and then the aqueous phase was further extracted with EtOAc. The combined organic phases were dried (MgSO$_4$), filtered, and concentrated in vacuo. Purification via flash column chromatography on silica gel (10% EtOAc in hexanes) gave the desired product (229.5 mg, 86%) as a yellow foamy solid: mp 157–158° C.; $R_f$=0.08 (20% EtOAc in hexanes); IR (neat) 3402, 3052, 1620 cm$^{-1}$; $^1$H NMR (400 MHz, CDCl$_3$) 8.87 (d, J=5.8 Hz, 1H), 7.99 (d, J=8.2 Hz, 1H), 7.83–7.72 (m, 5H), 7.47 (dd, J=8.1, 8.1 Hz, 1H), 7.26–7.20 (m, 2H), 6.97 (d, J=7.5 Hz, 1H), 6.92 (s, 2H), 6.79 (d, J=9.0 Hz, 1H), 5.30 (s, 1H), 2.31 (s, 3H), 2.26–2.10 (br s, 6H); $^{13}$C NMR (100 MHz, CDCl$_3$) 159.3, 143.6, 142.8, 137.2, 136.1 (2C), 135.6, 135.5, 134.3, 130.9, 130.1, 129.4 (2C), 128.9, 128.2, 128.0, 127.9, 127.8, 127.4, 126.8, 124.2, 122.3, 120.7, 116.8, 115.3, 21.2, 18.6; HRMS (CI, CH$_4$) Exact mass calcd for C$_{28}$H$_{24}$N$_2$ [M]$^+$ 388.1939, found 388.1925.

EXAMPLE 9

Preparation of 1-Np-IAN amine 1,2'-naphthylaniine (41.1 mg, 153 mol) and 1-chloroisoquinoline (25.1 mg, 153 mol) were dissolved in toluene (3.0 mL). AlMe$_3$ (0.23 mL, 2.0 M in toluene, 460 mol) was added in one portion via syringe and the solution was heated at reflux for 26 h. Then, the solution was cooled to room temperature and added to 6 M aqueous NaOH. Sodium potassium tartrate and EtOAc were added and the mixture was stirred for 30 min. The layers were separated and then the aqueous phase was further extracted with EtOAc. The combined organic phases were dried MgSO$_4$), filtered, and concentrated in vacuo. Purification via flash column chromatography on silica gel (10% EtOAc in hexanes) gave the desired product (59.1 mg, 97.7%) as a orange-yellow foam. A small amount seemed crystalline, but oiled out at 154–156° C.; $R_f$=0.06 (20% EtOAc in hexanes); IR (neat) 3393, 3053, 1619 cm$^{-1}$, $^1$H NMR (400 MHz, CDCl$_3$) 8.81 (d, J=5.6 Hz, 1H), 7.90 (d, J=8.3 Hz, 1H), 7.85 (d, J=8.3 Hz, 1H), 7.82–7.75 (m, 4H), 7.72 (d, J=8.3 Hz, 1H), 7.67 (dd, J=7.4, 7.4 Hz, 1H), 7.49 (d, J=8.9 Hz, 1H), 7.47–7.31 (m, 6H), 7.27 (dd, J=7.0, 7.0 Hz, 1H), 7.20 (dd, J=7.0, 7.0 Hz, 1H), 6.97 (d, J=8.3 Hz, 1H), 6.43 (s, 1H); $^{13}$C NMR (100 MHz, CDCl$_3$) 158.7, 143.3, 141.1, 138.6, 137.1, 134.8, 134.1, 130.9, 129.9, 129.1, 128.8, 128.6, 128.3, 128.2, 127.9, 127.7, 127.4, 126.9, 126.3, 126.1, 125.9, 124.9, 123.4, 123.3, 122.1, 120.9, 120.8, 119.0, 116.8; HRMS (CI, CH$_4$) Exact mass calcd for C$_{29}$H$_{20}$N$_2$ [M]$^+$ 396.1626, found 396.1611.

EXAMPLE 10

Preparation of 2-Np-IAN amine 2,2'-binaphthylamine (26.1 mg, 96.9 mol) and 1-chloroisoquinoline (15.8 mg, 96.6 mol) were dissolved in toluene (3.0 mL). AlMe$_3$ (0.075 mL, 2.0 M in toluene, 150 mol) was added in one portion via syringe and the solution was heated at reflux for 24 h. Then, the solution was cooled to room temperature and added to 6 M aqueous NaOH. Sodium potassium tartrate and EtOAc were added and the mixture was stirred for 30 min. The layers were separated and then the aqueous phase was further extracted with EtOAc. The combined organic phases were dried (MgSO$_4$), filtered, and concentrated in vacuo. Purification via flash column chromatography on silica gel (10% EtOAc in hexanes) gave the desired product (5.5 mg, 14%) as a brown oily residue: IR (neat) 3404, 3053, 1619 cm$^{-1}$; $^1$H NMR (400 MHz, CDCl$_3$) 8.79 (d, J=5.6 Hz, 1H), 7.92 (d, J=8.9 Hz, 2H), 7.86 (d, J=7.8 Hz, 1H), 7.81–7.79 (m, 2H), 7.69–7.64 (m, 4H), 7.59 (d, J=8.3 Hz, 1H), 7.41–7.28 (m, 5H), 7.23–7.20 (m, 1H), 7.11 (dd, J=8.9 Hz, 2.0 Hz, 1H), 6.95 (d, J=8.6 Hz, 1H), 6.23 (s, 1H); HRMS (CI, CH$_4$) Exact mass calcd for C$_{29}$H$_{20}$N$_2$ [M]$^+$ 396.1626, found 396.1705.

EXAMPLE 11

Other IAN-Amines

The IAN-amines listed in Table 2, below, are compounds of Formula II, which have been prepared from appropriate precursors according to the methods described herein.

TABLE 2

| R$^1$ | R$^2$ |
|---|---|
| H | H |
| H | CH$_2$C$_6$H$_5$ |
| H | CH(CH$_3$)$_2$ |
| H | C$_6$H$_5$ |
| H | 2,6-dimethylphenyl |
| H | 2,4,6-trimethylphenyl |
| H | 2,6-diisopropylphenyl |
| CH$_3$ | C(O)CH$_3$ |
| CH$_3$ | C(O)CH$_2$CH(OH)C$_6$H$_5$ |
| CH$_3$ | C(O)CH$_2$CH$_3$ |
| CH$_3$ | C(O)CH(CH$_3$)CH(OH)C$_6$H$_5$ |
| CH$_3$ | CH$_3$ |

EXAMPLE 12

Preparation of (Me-IAN)Zr(NMe$_2$)$_3$(HNMe$_2$)

The amine (10.5 mg, 37 μmol) and Zr(NMe$_2$)$_4$ (9.9 mg, 37 μmol) were weighed into a flame-dried vial in a glovebox. d$_8$-Toluene was then added and the clear red solution was transferred to a J-Young tube, sealed, and examined by $^1$H NMR, which revealed complete complexation. The solvent could be removed to give a red-orange powder: $^1$H NMR (400 MHz, d$_8$-toluene) δ 8.29 (d, J=6.2 Hz, 1H), 7.67 (d, J=9.1 Hz, 1H), 7.53 (d, J=7.9 Hz, 1H), 7.47 (d, J=8.6 Hz, 1H); 7.41 (d, J=9.1 Hz, 1H), 7.24 (d, J=8.0 Hz, 1H), 7.06 (d, J=6.2 Hz, 1H), 7.03–6.93 (m, 3H), 6.82 (dd, J=7.7, 7.7 Hz, 1H), 6.62 (dd, J=7.1, 7.1 Hz, 1H), 3.20 (s, 3H), 2.99 (s, 18H), 2.10 (d, J=6.3 Hz, 6H); $^{13}$C NMR (100 MHz, d$_8$-toluene) ppm 158.3, 151.2, 139.8, 136.9, 136.0, 132.3, 131.0, 130.8, 128.6, 128.4, 127.1, 126.7, 126.6, 126.5, 125.7, 121.6, 119.4, 117.8, 114.3, 43.1, 38.9, 38.1.

EXAMPLE 13

Preparation of (Me-IAN)$_2$Zr(NMe$_2$)$_2$

The amine (22.7 mg, 80 μmol) and Zr(NMe$_2$)$_4$ (10.7 mg, 40 μmol) were weighed in a flame-dried vial within a glovebox. d$_8$-Toluene was added, giving a clear red solution that was transferred to a J-Young tube, sealed, and warmed to 80° C. for 12 hours. Analysis by $^1$H NMR revealed complete consumption of the amine and formation of a single compound, an orange-red powder after removal of solvent: $^1$H NMR (400 MHz, d$_8$-toluene) δ 7.88 (d, J=6.2 Hz, 1H), 7.69 (d, J=9.0 Hz, 1H), 7.50 (d, J=9.0 Hz, 1H), 7.33 (d, J=7.8 Hz, 1H), 7.17 (d, J=8.6 Hz, 1H), 6.88 (d, J=8.0 Hz, 1H), 6.80 (d, J=6.2 Hz, 1H), 6.71 (ddd, J=7.5, 7.5, 1.1 Hz, 1H), 6.70 (ddd, J=7.5, 7.5, 1.1 Hz, 1H), 6.52 (ddd, J=7.5, 7.5, 1.2 Hz, 1H), 6.36 (ddd, J=7.5, 7.5, 1.2 Hz, 1H), 6.03 (d, J=8.5 Hz, 1H), 3.67 (s, 3H), 2.95 (s, 6H), 2.15 (d, J=6.4 Hz, 3H); $^{13}$C NMR (100 MHz, d$_8$-toluene) ppm 158.7, 154.5, 139.2, 136.1, 135.3, 131.1, 130.6, 130.0, 127.7, 127.5, 126.3 (2c), 126.1, 125.5 (2c), 121.0, 118.2, 117.5, 116.5, 45.3, 38.9, 37.7.

EXAMPLE 14

Preparation of (Me$_2$-IAN)FeCl$_2$(NCCH$_3$)

Figure 3:
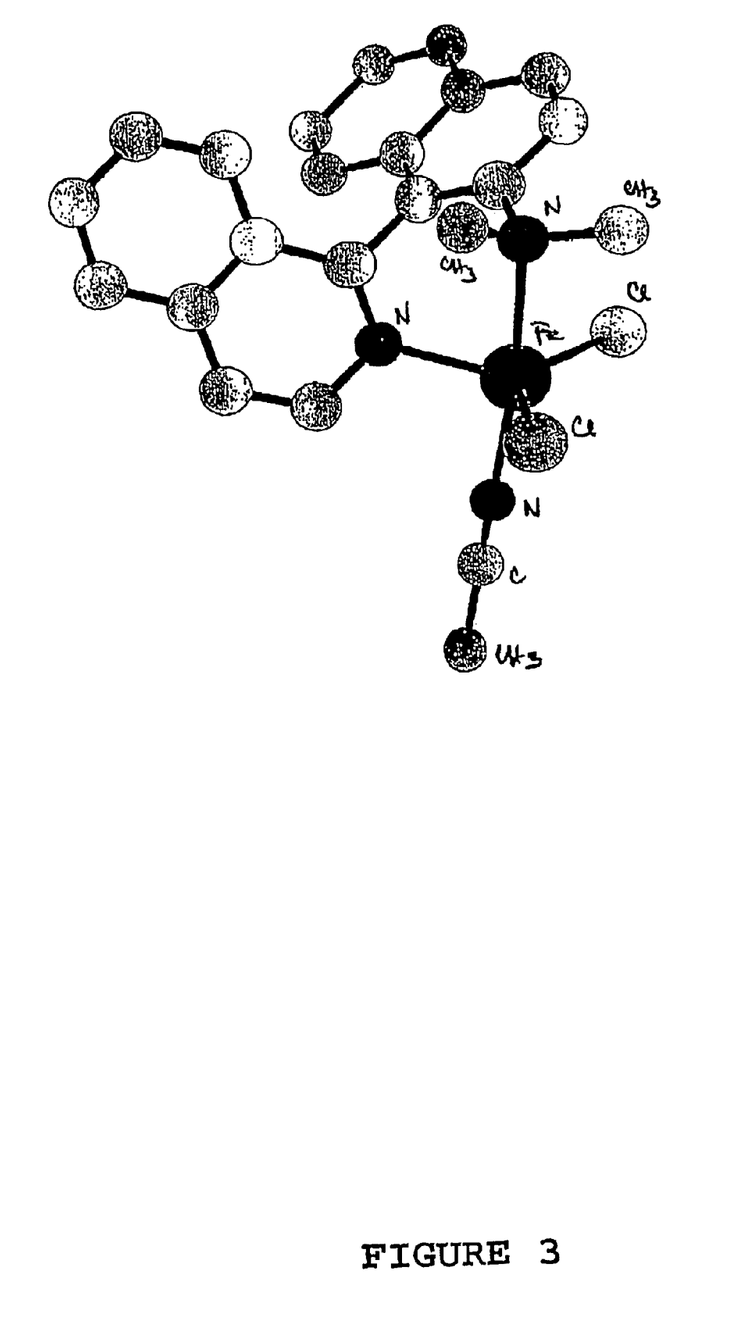
FIG. 3 is an ORTEP rendition of the crystal structure of $(Me_2-IAN)FeCl_2(NCCH_3)$.

A solution of iron (II) chloride hydrate was heated at reflux for two days prior to the addition of Me2-IAN (1 equiv.). The reaction mixture was heated at reflux for an additional two days. Upon cooling, orange crystals formed over a 12 hour period. The crystals were of X-ray diffraction quality; upon analysis, their structure was solved as (Me$_2$-IAN)FeCl$_2$(NCCH$_3$), and is shown in FIG. 3.

EXAMPLE 15

Preparation of rac-(Me-IANamine)$_2$Zr(NMe$_2$)$_2$

Me-IANamine (300 mg, 1.05 mmol) and Zr(NMe$_2$)$_4$ (142 mg, 0.53 mmol) were weighed into a flame-dried vial within a glovebox. Toluene-d$_8$ was added to yield a clear red solution that was transferred to a J-Young tube. J-Young tubes are available from J.YOUNG (Scientific Glassware) Ltd., of London (United Kingdom), or through Wilmad-Labglass of Buena, N.J. The tube was sealed and warmed to 80° C. for 12 h. Analysis by $^1$H NMR revealed complete consumption of the amine and formation of a single compound, which was an orange-red powder after removal of solvent: $^1$H NMR (400 MHz, d$_8$-toluene) d 7.88 (d, J=6.2 Hz, 2H), 7.69 (d, J=9.0 Hz, 2H), 7.50 (d, J=9.0 Hz, 2H), 7.33 (d, J=7.8 Hz, 2H), 7.17 (d, J=8.6 Hz, 2H), 6.88 (d, J=8.0 Hz, 2H), 6.80 (d, J=6.2 Hz, 2H), 6.71 (ddd, J=7.5, 7.5, 1.1 Hz, 2H), 6.70 (ddd, J=7.5, 7.5, 1.1 Hz, 2H), 6.52 (ddd, J=7.5, 7.5, 1.2 Hz, 2H), 6.36 (ddd, J=7.5, 7.5, 1.2 Hz, 2H), 6.03 (d, J=8.5 Hz, 2H), 3.67 (s, 6H), 2.95 (s, 12H); $^{13}$C NMR (100 MHz, $d_8$-toluene) d 158.7, 154.5, 139.2, 136.1, 135.3, 131.1, 130.6, 130.0, 127.7, 127.5, 126.3 (2C), 126.1, 125.5 (2C), 121.0, 118.2, 117.5, 116.5, 45.3, 37.7. X-ray quality single-crystals were grown from $d_6$-benzene by slow evaporation.

EXAMPLE 16

Preparation of (Me-IANamine)$_2$ZrCl$_2$

Route 1: Me-IANamine (300 mg, 1.05 mmol) and Zr(NMe$_2$)$_4$ (142 mg, 0.53 mmol) were combined in a glass vial, dissolved in toluene, and transferred to a J-Young tube. The clear, red solution was heated at 80° C. for 12 h. The solution was then transferred to a round bottom flask and Me$_2$NH.HCl (75.3 mg, 0.92 mmol) was added. Trimethylsilyl chloride (TMSCl) effected the same reaction as Me$_2$NH.HCl at 0° C. Volatiles were removed in vacuo after 2 h to yield an orange, powdery residue. An X-ray diffraction quality crystal was obtained from a diffusion chamber of toluene and hexane.

Route 2: Me-IANamine (150 mg, 529 mmol) and LiNMe$_2$ (26.9 mg, 527 mmol) were combined in a vial and dissolved in toluene. The opaque purple solution was allowed to rest at room temperature for 30 min, and then the solvent and volatiles were removed in vacuo. The residue was re-dissolved in toluene and ZrCl$_4$ (61.5 mg, 264 mmol) was added. After 30 min at room temperature, a red solution and orange precipitate of the product resulted.

EXAMPLE 17

Preparation of (Me-IAN)ZrMe$_3$

Me-IAN amine (8.5 mg, 29.9 μmol) and Zr(NMe$_2$)$_4$ (8.0 mg, 29.9 μmol) were weighed into a flame-dried vial in a glovebox. Toluene was then added and the clear red solution was transferred to a J-Young tube. Solvent and other volatiles were removed in vacuo and the red oily residue, (Me-IAN)Zr(NMe$_2$)$_3$, was redissolved in toluene. AlMe$_3$ (0.09 mL, 180 μmol, 6 equiv.) were added to the toluene solution in one portion via syringe. The red solution immediately changed to a light orange, clear solution. After 1 h, a dark, cherry-red solution was present. Solvent was removed in vacuo and the oily residue was re-dissolved in $d_6$-benzene. Analysis by $^1$H NMR spectroscopy showed complete conversion to the desired product.

EXAMPLE 18

Preparation of (2,4,6-Me$_3$Ph-IAN)ZrCl$_3$ 2,4,6-Me$_3$Ph-IAN amine (20.4 mg, 52.5 μmol) and LiNMe$_2$ (2.9 mg, 56.8 μmol) were combined in a vial and dissolved in toluene. The opaque purple solution was allowed to sit at room temperature for 30 min and then the solvent and other volatiles were removed in vacuo. The residue was re-dissolved in $d_6$-benzene and ZrCl$_4$ (12.2 mg, 52.4 μmol) was added. After 1 h at room temperature, a red solution and orange precipitate of (2,4,6-Me$_3$Ph-IAN)ZrCl$_3$ resulted. The product was characterized by $^1$H NMR spectroscopy, which showed that the only impurity present was starting material.

EXAMPLE 19

Preparation of (2,6-iPr$_2$Ph-IAN)Zr(NMe$_2$)$_3$ 2,6-iPr$_2$Ph-IAN amine (18.9 mg, 43.9 mol) and Zr(NMe$_2$)$_4$ (11.9 mg, 44.5 mol) were weighed into a flame-dried vial in a glovebox. $d_6$-Benzene was then added and the clear red-orange solution was transferred to a J-Young tube. $^1$H NMR, taken 5 min after mixing, revealed complete complexation. $^1$H NMR (400 MHz, C$_6$D$_6$) 8.31 (d, J=6.2 Hz, 1H), 7.52–7.48 (m, 2H), 7.43 (d, J=9.3 Hz, 1H), 7.32 (dd, J=7.8, 1.5 Hz, 1H), 7.29 (d, J=8.3 Hz, 1H), 7.18–7.11 (m, 3H), 7.10–6.95 (m, 4H), 6.90 (ddd, J=8.3, 8.3, 1.2 Hz, 1H), 6.65 (ddd, J=7.0, 7.0, 1.2 Hz, 1H), 3.63 (sept, J=6.8 Hz, 1H), 2.85 (s, 18 H), 2.27 (sept, J=6.8 Hz, 1H), 1.45 (d, J=6.8 Hz, 3H), 1.44 (d, J=6.8 Hz, 3H), 0.65 (d, J=6.8 Hz, 3H), 0.51 (d, J=6.8 Hz, 3H); $^{13}$C NMR (100 MHz, C$_6$D$_6$) 158.2, 152.3, 146.8, 146.7, 145.0, 138.3, 137.1, 136.6, 131.3, 3730.9, 130.5, 128.6, 127.3, 126.8, 126.7 (2C), 126.2, 125.2, 124.2, 123.8, 122.6, 122.1, 119.4, 109.7, 43.1 (6C), 28.6, 28.0, 26.5, 25.0, 24.6, 22.8.

EXAMPLE 20

Preparation of (2,6-Me$_2$Ph-IAN)Zr(NMe$_2$)$_3$ 2,6-Me$_2$Ph-IAN amine (9.5 mg, 25.4 mol) and Zr(NMe$_2$)$_4$ (6.8 mg, 25.4 mol) were weighed into a flame-dried vial in a glovebox. $d_6$-Benzene was then added and the clear red-orange solution was transferred to a J-Young tube. A $^1$H NMR spectrum, taken 5 min after mixing, revealed formation of the desired complex in 100% yield. $^1$H NMR (400 MHz, C$_6$D$_6$) 8.37 (d, J=6.3 Hz, 1H), 7.57 (d, J=8.6 Hz, 1H), 7.50 (d, J=7.9 Hz, 1H), 7.45 (d, J=9.3 Hz, 1H), 7.32 (d, J=8.2 Hz, 1H), 7.24 (d, J=7.1 Hz, 1H), 7.09–7.05 (m, 3H), 6.99–6.94 (m, 3H), 6.87 (d, J=8.5 Hz, 1H), 6.82–6.78 (m, 1H), 6.70 (ddd, J=7.8, 7.8, 1.3 Hz, 1H), 2.79 (s, 18H), 2.42 (s, 3H), 1.92 (s, 3H); $^{13}$C NMR (100 MHz, C$_6$D$_6$) 167.0, 148.2, 139.7, 136.5, 131.2, 131.1, 130.9, 129.3 (2C), 128.9, 128.5, 128.0, 127.2, 126.4, 126.1 (2C), 126.0, 124.4, 121.8 (2C), 119.3, 118.0, 112.5, 43.1 (6C), 19.1, 18.7.

EXAMPLE 21

Preparation of (2,4,6-Me$_3$Ph-IAN)Zr(NMe$_2$)$_3$ 2,4,6-Me$_3$Ph-IAN amnine (12.7 mg, 32.7 mol) and Zr(NMe$_2$)$_4$ (8.8 mg, 32.9 mol) were weighed into a flame-dried vial in a glovebox. $d_6$-Benzene was then added and the clear red-orange solution was transferred to a J-Young tube. A $^1$H NMR spectrum, taken 5 min after mixing, revealed formation of the desired complex in 100% yield. $^1$H NMR (400 MHz, C$_6$D$_6$) 8.39 (d, J=6.2 Hz, 1H), 7.58 (d, J=8.6 Hz, 1H), 7.52–7.48 (m, 2H), 7.33 (d, J=8.1 Hz, 1H), 7.11–7.01 (m, 4H), 6.97 (ddd, J=6.8, 6.8, 1.3 Hz, 1H), 6.90–6.87 (m, 2H), 6.81 (ddd, J=7.7, 7.7, 1.3 Hz, 1H), 6.71 (ddd, J=7.0, 7.0, 1.3 Hz, 1H), 2.82 (s, 18H), 2.42 (s, 3H), 2.22 (s, 3H), 1.91 (s, 3H); $^{13}$C NMR (100 MHz, C$_6$D$_6$) 161.1, 151.1, 145.2, 139.7, 137.3, 136.8, 136.5, 134.5, 133.1, 131.2, 131.0, 130.9, 129.6, 129.3, 128.1, 128.0, 127.3 (2C), 127.1, 126.4, 126.0, 125.9, 121.8, 119.4, 117.9, 112.6, 43.1 (6C), 20.8, 19.0, 18.6.

EXAMPLE 22

Preparation of (1-Np-IAN)Zr(NMe$_2$)$_3$

1-Np-IAN amine (17.0 mg, 42.9 mol) and Zr(NMe$_2$)$_4$ (11.5 mg, 43.0 mol) were weighed into a flame-dried vial in a glovebox. $d_6$-Benzene was then added and the clear red-orange solution was transferred to a J-Young tube. A $^1$H NMR spectrum, taken 5 min after mixing, revealed formation of the desired complex in 100% yield. $^1$H NMR (400 MHz, $C_6D_6$) 8.26 (d, J=6.2 Hz, 1H), 7.82 (d, J=7.3 Hz, 1H), 7.71 (d, J=8.6 Hz, 1H), 7.52 (d, J=7.8 Hz, 1H), 7.51 (d, J=7.8 Hz, 1H), 7.47 (d, J=8.6 Hz, 1H), 7.40 (d, J=7.8 Hz, 1H), 7.39 (d, J=8.1 Hz, 1H), 7.33 (d, J=9.1 Hz, 1H), 7.26 (d, J=8.1 Hz, 1H), 7.17 (d, J=9.1 Hz, 1H), 7.13 (d, J=8.3 Hz, 1H), 7.08 (d, J=7.0 Hz, 1H), 7.05 (d, J=5.6 Hz, 1H), 7.00 (ddd, J=7.0, 7.0, 1.0 Hz, 1H), 6.94–6.87 (m, 2H), 6.78 (ddd, J=7.0, 7.0, 1.1 Hz, 1H), 6.59 (ddd, J=7.0, 7.0, 1.1 Hz, 1H), 2.97 (s, 18H); $^{13}$C NMR (100 MHz, $C_6D_6$) 157.4, 149.2, 149.1, 139.9, 137.1, 136.4, 135.2, 132.0, 131.0, 129.7, 128.6 (2C), 128.4 (2C), 127.7, 127.1, 126.8, 126.7, 126.1, 125.2, 125.1, 124.9, 124.3, 123.2, 122.3, 122.1, 120.7, 119.0, 43.1 (6C).

EXAMPLE 23

Preparation of (Ph-IAN)$_2$Zr(NMe$_2$)$_2$

Ph-IAN amine (20.2 mg, 58.3 mol) and Zr(NMe$_2$)$_4$ (7.8 mg, 29.2 mol) were combined in a flamed dried vial in a glovebox. Benzene was added and the clear red solution was transferred to a J-Young tube and heated in an oil bath at 60° C. for 18 h. The solvent was removed in vacuo, leaving the desired product as a red powder. $^1$H NMR (400 MHz, $C_6D_6$) 8.77 (d, J=6.2 Hz, 2H), 7.45–7.35 (m, 4H), 7.30–7.19 (m, 6H), 7.10–7.02 (m, 4H), 6.96 (d, J=6.2 Hz, 2H), 6.91–6.80 (m, 6H), 6.71–6.63 (m, 4H), 6.52 (dd, J=8.1, 8.1 Hz, 2H), 6.16 (dd, J=8.1Hz, 2H), 5.51 (d, J=8.6Hz, 2H), 2.74 (s, 12H). $^{13}$C NMR (100 MHz, $C_6D_6$) 159.2, 155.9, 153.0, 140.4, 136.1, 134.3, 130.7, 130.0 (2C), 128.9 (2C), 128.2, 127.9, 127.5, 127.1, 127.0, 126.5, 126.0, 125.7, 124.1 (2C), 122.7, 120.1, 119.1, 46.5 (2C).

EXAMPLE 24

Preparation of (Ph-IAN)$_2$ZrMe$_2$ (Ph-IAN)$_2$Zr(NMe$_2$)$_2$ (21.1 mg, 24.2 mol) was dissolved in toluene and then AlMe$_3$ (4 equiv., 0.05 mL, 100 mol) were added in one portion via syringe. Upon addition, the dark red solution changed to a light orange, clear solution. After 3 h, a dark, cherry-red solution was present. Solvent was removed in vacuo and the oily residue was re-dissolved in d$_6$-benzene. A $^1$H NMR spectrum showed complete conversion to the desired product. $^1$H NMR (400 MHz, $C_6D_6$) 7.98 (d, J=6.3 Hz, 2H), 7.72 (d, J=8.6 Hz, 2H), 7.64 (d, J=9.2 Hz, 2H), 7.49 (d, J=7.0 Hz, 2H), 7.48 (d, J=9.2 Hz, 2H), 7.29 (d, J=7.9 Hz, 4 Hz), 7.19 (d, J=7.6 Hz, 4H), 7.16–7.08 (m, 2H), 7.06–7.00 (m, 4H), 6.95–6.82 (m, 8H), 6.77–6.70 (m, 2H), –0.56 (s, 6H), $^{13}$C NMR (100 MHz, $C_6D_6$) 157.9, 149.9, 137.2, 136.2, 135.2, 132.3, 132.0, 131.1, 129.4 (2C), 128.4 (3C), 127.8, 126.8, 126.4, 125.7, 124.2 (2C), 123.7, 123.0, 121.4, 120.4, 115.0, 1.2.

EXAMPLE 25

Preparation of (Bn-IAN)$_2$ZrMe$_2$ (Bn-IAN)$_2$Zr(NMe$_2$)$_2$ (38.1 mg, 42.4 mol) was dissolved in toluene, and then AlMe$_3$ (4 equiv., 0.08 mL, 160 mol) were added in one portion via syringe. Upon addition, the dark red solution changed to a light orange, clear solution. After 1 h, a dark, cherry-red solution was present. Solvent was removed in vacuo and the oily residue was re-dissolved in d$_6$-benzene. A $^1$H NMR spectrum showed complete conversion to the desired product. $^1$H NMR (400 MHz, $C_6D_6$) 7.97 (d, J=6.2 Hz, 2H), 7.49 (d, J=8.7 Hz, 2H), 7.46 (d, J=7.3 Hz, 2H), 7.44 (d, J=8.9 Hz, 2H), 7.28 (d, J=9.2 Hz, 2H), 7.24 (d, J=7.5 Hz, 4H), 7.13–7.09 (m, 2H), 7.06–7.03 (m, 4H), 6.98–6.91 (m, 8H), 6.87 (d, J=6.2 Hz, 2H), 6.79 (dd, J=7.3, 7.3 Hz, 2H), 6.57 (dd, J=7.3, 7.3 Hz, 2H), 4.70 (d, J=8.4 Hz, 4H), –0.47 (s, 6H); $^{13}$C NMR (100 MHz, $C_6D_6$) 158.3, 142.2, 137.1, 135.5, 132.8, 131.6(2C), 128.6 (3C), 128.3, 127.5, 126.9 (3C), 126.7, 126.6 (3C), 126.4, 125.7, 121.8, 119.7, 119.1, 50.9.

EXAMPLE 26

Mediation of an Enantioselective Ethylation: Benzaldehyde to 1-Hydroxy-1-phenylpropane (+)-Me-IAN amine (19.0 mg, 66.8 μmol) was dissolved in toluene (0.85 mL) in a 10 mL flask. Et$_2$Zn (1.22 mL, 1.1 M in toluene, 1.34 mmol) was added in one portion via syringe. Immediately, a clear red-orange solution formed. After stirring for 30 min., benzaldehyde (0.068 mL, 0.669 mmol) was added. This addition immediately lightened the solution to a pale orange-yellow. After 19 h, the solution returned to its red-orange color. Water was added and the mixture was extracted three times with CH$_2$Cl$_2$. The combined organic phases were dried over MgSO$_4$, filtered, and concentrated iii vacuo. Purification of the crude product via flash column chromatography on silica gel gave 1-hydroxy-1-phenylpropane as a light yellow liquid (28.6 mg, 31.4%). HPLC analysis of the product (OD column, 1.0 mL/min, 2% iPrOH in hexanes) gave 85.2% ee (retention time of major peak=13.7 min, retention time of minor peak=16.3 min) and a decrease in the ee of (+)-Me-IAN amine (from 99% to 93.2% ee).

EXAMPLE 27

General Procedure for Ethylene Polymerization with (R-IAN)$_2$ZrL$_2$ Precatalysts A 1 L reactor was charged with activator (MMAO), tri-isobutyl aluminum (10–40% relative to activator), and ethylene at the prescribed pressure (135–200 psi) and temperature (70–85° C.). The activator MMAO differs from MAO in that a portion of the methyl groups of MAO have been substituted with isobutyl groups in MMAO. Tri-isobutyl aluminum (TIBA) acts as a scavenger for water and other Lewis bases that could reduce the activity of the polymerization catalyst.

A solution of the (R-IAN)$_2$ZrL$_2$ precatalyst and MMAO activator was then added to the reactor via pressure injection. Following the reaction period (30–40 min), the reaction was quenched by addition of methanol. The solvent was removed, and the polymer was dried and analyzed.

The polymerization conditions and results are summarized in Table 3, below.

TABLE 3

Polymerization Conditions and Results

| Precatalyst | Catalyst (umol) | Activator umol (1) | Scavenger (umol) | Al/Zr (1) | Ethylene (psl) | Temperature (C.) | Time (h) | Polymer yield (g) | Activity (2) | Activity (3) |
|---|---|---|---|---|---|---|---|---|---|---|
| (Me-IAN)$_2$ZrCl$_2$ | 2.6 | 2600 | 1000 | 985 | 135 | 85 | 0.67 | 3.6 | 221.6 | 1507.6 |
| (Me-IAN)$_2$ZrCl$_2$ | 2.6 | 2600 | 1000 | 985 | 135 | 85 | 0.67 | 3.6 | 221.6 | 1507.6 |
| (Me-IAN)$_2$ZrCl$_2$ | 5.2 | 5200 | 1000 | 1000 | 135 | 85 | 0.67 | 7.5 | 234.4 | 1594.6 |
| (Me-IAN)$_2$ZrMe$_2$ | 3.6 | 3600 | 1000 | 1000 | 135 | 85 | 0.67 | 0 | 0 | 0 |
| (Me-IAN)$_2$ZrMe$_2$ | 7.2 | 7200 | 1000 | 1000 | 135 | 85 | 0.67 | 2.3 | 51.9 | 353.2 |
| (Ph-IAN)$_2$ZrMe$_2$ | 2 | 2000 | 2000 | 1000 | 200 | 70 | 0.5 | 13 | 955.5 | 6500 |
| (Ph-IAN)$_2$ZrMe$_2$ | 2 | 2000 | 2000 | 1000 | 200 | 70 | 0.5 | 8.5 | 624.8 | 4250 |
| (Ph-IAN)$_2$ZrMe$_2$ | 1 | 1000 | 2000 | 1000 | 200 | 70 | 0.5 | 1.9 | 279.3 | 1900 |
| (Bn-IAN)$_2$ZrMe$_2$ | 2 | 2000 | 2000 | 1000 | 200 | 70 | 0.5 | 12.4 | 911.4 | 6200 |
| (Bn-IAN)$_2$ZrMe$_2$ | 2 | 2000 | 2000 | 1000 | 200 | 70 | 0.5 | 4.8 | 352.8 | 2400 |

Notes:
(1) Calculated without respect to degree of isobutylation.
(2) g/mmol/hr/atm
(3) g/mmol/hr/100 psi The entire disclosures of the patents and publications mentioned herein are incorporated by reference in the present specification.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound of the formula wherein $R^1$, $R^2$, and $R^7$ each represents hydrogen, halogen, or a substituted or unsubstituted radical independently selected from the group consisting of alkyl, cycloalkyl, aryl, aralkyl, heterocyclo, acyl, and $SiR_aR_bR_c$;

alternatively, $R^1$ and $R^2$, when taken together, form a $=CR_aR_b$ group;

or, when taken together with the nitrogen atom to which they are attached, $R^1$ and $R^2$ form a heterocyclic ring structure, which may be unsubstituted or substituted; and $R_a$, $R_b$, and $R_c$ each represents hydrogen, halogen, or a substituted or unsubstituted radical independently selected from the group consisting of alkyl, cycloalkyl, aryl, aralkyl, heterocyclo, and acyl.

2. A process for the synthesis of a compound of formula wherein $R^1$, $R^2$, and $R^7$ each represents hydrogen, halogen, or a substituted or unsubstituted radical independently selected from the group consisting of alkyl, cycloalkyl, aryl, aralkyl, heterocyclo, acyl, and $SiR_aR_bR_c$;

alternatively, $R^1$ and $R^2$, when taken together, form a $=CR_aR_b$ group;

or, when taken together with the nitrogen atom to which they are attached, $R^1$ and $R^2$ form a heterocyclic ring structure, which may be unsubstituted or substituted; and $R_a$, $R_b$, and $R_c$ each represents hydrogen, halogen, or a substituted or unsubstituted radical independently selected from the group consisting of alkyl, cycloalkyl, aryl, aralkyl, heterocyclo, and acyl;

comprising reacting a compound of formula with a compound of formula wherein LG is a leaving group,
in the presence of an aluminum compound.

3. The process of claim 2 wherein one of $R^1$ and $R^2$ represents hydrogen.

4. The process wherein the aluminum compound is a dialkyl aluminum chloride or trimethyl aluminum.

5. A complex of a compound of claim 1 with a metal atom or with a proton.

6. The complex of claim 5, wherein the metal atom is a group IV metal.

7. The complex of claim 5, wherein the metal is zirconium, zinc, or iron.

* * * * *